(12) United States Patent
Kunz et al.

(10) Patent No.: US 9,179,982 B2
(45) Date of Patent: Nov. 10, 2015

(54) METHOD AND SYSTEM FOR AUTOMATIC PATIENT IDENTIFICATION

(75) Inventors: Patrik Kunz, Baden (CH); Jonas Honegger, Zurich (CH); Michael Huber, Beinwil am See (CH)

(73) Assignee: Varian Medical Systems, Inc., Palo Alto, CA (US)

( * ) Notice: Subject to any disclaimer, the term of this patent is extended or adjusted under 35 U.S.C. 154(b) by 227 days.

(21) Appl. No.: 13/424,560

(22) Filed: Mar. 20, 2012

(65) Prior Publication Data

US 2013/0251099 A1 Sep. 26, 2013

(51) Int. Cl.
| | |
|---|---|
| G06K 9/00 | (2006.01) |
| A61B 19/00 | (2006.01) |
| A61B 5/117 | (2006.01) |
| A61N 5/10 | (2006.01) |
| G06F 19/00 | (2011.01) |
| A61B 5/00 | (2006.01) |

(52) U.S. Cl.
CPC ............... *A61B 19/44* (2013.01); *A61B 5/117* (2013.01); *A61N 5/1048* (2013.01); *G06K 9/00885* (2013.01); *A61B 5/0033* (2013.01); *G06F 19/3456* (2013.01); *G06K 2209/05* (2013.01)

(58) Field of Classification Search
USPC ............... 382/100, 115, 117, 118, 124–132; 128/922; 378/4–27
See application file for complete search history.

(56) References Cited

U.S. PATENT DOCUMENTS

| | | | |
|---|---|---|---|
| 4,857,716 A | 8/1989 | Gombrich et al. | |
| 7,251,353 B2 * | 7/2007 | Doi et al. ...................... | 382/128 |
| 7,454,041 B2 * | 11/2008 | Sukegawa et al. ............ | 382/118 |
| 8,019,042 B2 * | 9/2011 | Shukla et al. .................. | 378/65 |
| 8,135,201 B2 * | 3/2012 | Smith et al. .................... | 382/132 |
| 2003/0083562 A1 * | 5/2003 | Bani-Hashemi et al. ..... | 600/407 |
| 2004/0101180 A1 * | 5/2004 | Doi et al. ...................... | 382/128 |
| 2007/0031010 A1 * | 2/2007 | Sukegawa et al. ............ | 382/118 |
| 2007/0291895 A1 * | 12/2007 | Yin et al. ........................ | 378/20 |
| 2009/0262894 A1 * | 10/2009 | Shukla et al. .................. | 378/65 |

OTHER PUBLICATIONS

Palmgren et al., "Fingerprint recognition to assist daily identification of radiotherapy patients," Journal of Radiotherapy in Practice (2009) 8, pp. 17-22.
Wu et al., "A neural network based 3D/3D image registration quality evaluator for the head-and-neck patient setup in the absence of a ground truth," Med. Phys. 37(11), Nov. 2010, pp. 5756-5764.
Roshni VS et al., "Using mutual information and cross correlation as metrics for registration of images, Journal of Theoretical and Applied Information Technology," 2008, pp. 474-481.

* cited by examiner

*Primary Examiner* — Anand Bhatnagar
(74) *Attorney, Agent, or Firm* — Houst Consulting

(57) ABSTRACT

In a method of verifying patient identity, an image of an individual who is to receive radiotherapy is obtained and compared with a reference image of a patient to whom the radiotherapy is intended. Confirmation or negation of the individual to be the patient intended can be made based on the comparison of the image of the individual with the reference image of the patient.

22 Claims, 3 Drawing Sheets

METHOD AND SYSTEM FOR AUTOMATIC PATIENT IDENTIFICATION

BACKGROUND

This disclosure relates in general to radiation systems and methods and in particular to methods and systems for patient identification using medical images.

Patient identification confirms or negates the identity of a patient to whom radiotherapy is intended or planned. It is an important process to prevent accidental mistreatment, especially in fractionated radiotherapy where the total treatment dose is delivered in multiple sessions over time. To prevent patient mismatches, radiotherapy centers usually implement workflow processes and guidelines for patient identification. These processes can be as simple as asking control questions such as the patient's name and date of birth etc. Some more sophisticated processes use barcode or fingerprint recognition systems. These and other conventional patient identification processes are implemented as a step separate from the treatment and are more or less prone to errors. For instance, patients may have the same or similar names and the illness or anxiety may hinder them to respond to their own names. The control questions may be easily omitted, especially in situations where the daily treatment plan is delayed and multiple patients are waiting or patients need to be rescheduled to other treatment systems. The barcode or fingerprint recognition systems may lead to residual errors as the patient barcode or fingerprint may be checked too early before the patient is actually positioned in the treatment room for treatment.

There is therefore a need for a patient identification system with improved accuracy and robustness in general. There is a need for a method that can be integrated with existing patient identification systems to verify the correctness of the identification process. There is a need for a patient identification system which can be implemented as an integral part of the treatment process and automatically performed to reduce the risks of exchanging patients by mistakes between activities.

SUMMARY

Methods and systems for patient identification using medical images are provided. Radiotherapy methods and systems including patient identification as an integral part of the radiotherapy are also provided. Other embodiments are described further herein.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION

Figure 1:
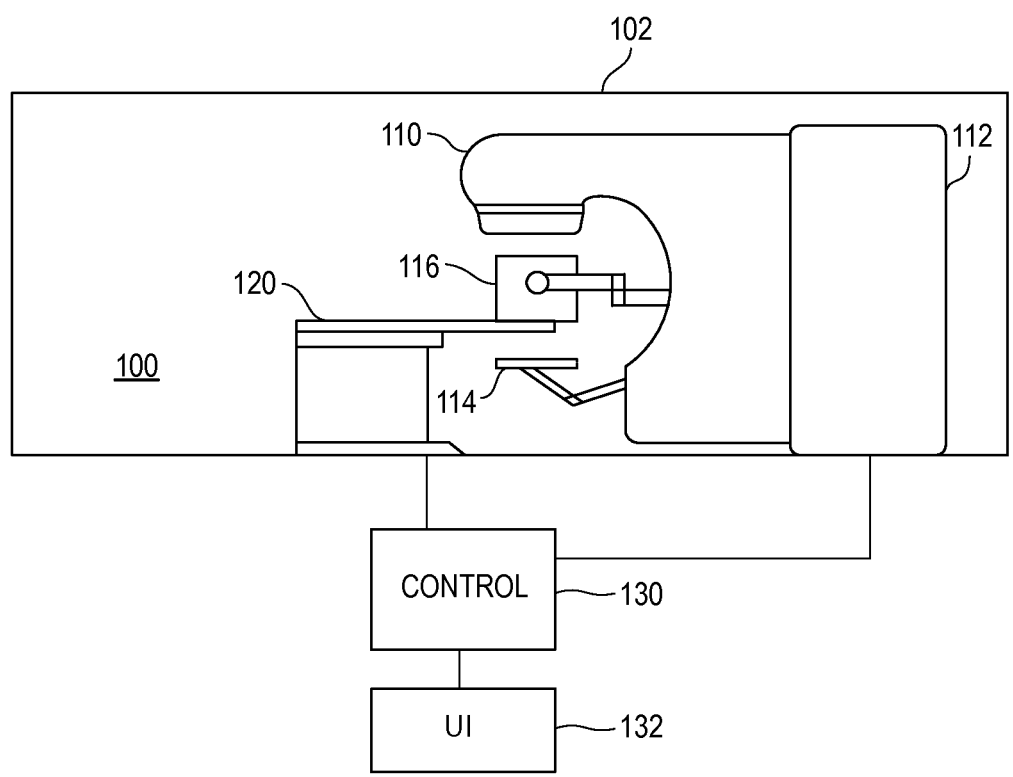
FIG. 1 is a schematic representation of an exemplary radiation system in accordance with some embodiments of the disclosure.

Various embodiments of patient identification methods and systems are described. It is to be understood that the disclosure is not limited to the particular embodiments described as such which may, of course, vary. An aspect described in conjunction with a particular embodiment is not necessarily limited to that embodiment and can be practiced in any other embodiments. For instance, while various patient identification methods and systems are described in connection with x-ray imaging, it will be appreciated that the methods and systems can also be implemented in other imaging modalities. It is also to be understood that the terminology used herein is for the purpose of describing particular embodiments only, and is not intended to be limiting since the scope of the disclosure will be limited only by the appended claims, along with the full scope of equivalents to which such claims are entitled. As used in the description and appended claims, the singular forms of "a," "an," and "the" include plural references unless the context clearly dictates otherwise. Thus, for example, reference to "an image of an individual" may include one or more images of an individual, and reference to "the reference image of the patient" may include one or more reference images of the patient.

As used herein, the term "image" or "medical image" may be used interchangeably and refers to an image created by an imaging system, which includes but is not limited to x-ray radiography, X-ray computed tomography (CT) imaging, magnetic resonance imaging (MRI), positron emission tomography (PET) imaging, single photon emission computed tomography (SPECT) imaging, and ultrasound (US) imaging. A medical image can be either a 2D image or a 3D image.

The present disclosure provides a patient identification method using medical images acquired as part of daily patient setup. The patient identification process can be implemented as an integral part of the treatment process and performed automatically. The patient identification process can be conducted after the patient has been positioned on the treatment table and immediately before the treatment beam is turned on for irradiation. The short time window between the patient identification and the delivery of treatment dose inherently reduces the risk of exchanging patients by mistakes between activities.

In some embodiments, a method of verifying a patient identity using medical images is provided. Medical Image of an individual who is to receive radiotherapy is obtained using an imaging system. The obtained image of the individual can be compared with a reference image of the patient to whom the radiotherapy is intended or planned. The reference image of the patient can be obtained in a planning session or in the first treatment session in fractionated radiotherapy. A confirmation or negation that the individual who is to receive radiotherapy is the patient intended can be made based on the comparison of the image of the individual with the reference image of the patient.

The medical image of the individual can be obtained using an imaging system located in a room designated for patient identification. Alternatively, the medical image of the individual can be obtained using an imaging system located in the treatment room. For example, an imaging system can be coupled to a treatment machine. Alternatively, an imaging system can be separated from a treatment machine but still located in the treatment room. One advantage of verifying patient identity in the treatment room is that the patient can remain in the treatment room after the identity verification, and as such, the risk of exchanging patients by mistakes can be greatly reduced.

The medical images of the individual can be obtained using any suitable imaging modalities such as X-ray radiography, computed tomography (CT) imaging, magnetic resonance imaging (MRI), positron emission tomography (PET) imaging, single photon emission computed tomography (SPECT) imaging, and ultrasound (US) imaging. Likewise, the reference images of the patient to whom the radiotherapy is planned or intended can be obtained using any suitable imaging modalities such as X-ray radiography, computed tomography (CT) imaging, magnetic resonance imaging (MRI), positron emission tomography (PET) imaging, single photon emission computed tomography (SPECT) imaging, and ultrasound (US) imaging. The medical image of the individual and the reference image of the patient may be obtained using a same imaging modality at different locations and times. For example, the images of both the individual and the patient may be obtained using x-ray imaging, although the images may be acquired with different x-ray imaging machines. Alternatively, the medical image of the individual and the reference image of the patient may be obtained using different imaging modalities. For example, the medical image of the individual to receive radiotherapy may be obtained using x-ray imaging, whereas the reference image of the patient may be obtained using MRI or other imaging modalities, or vice versa.

These and other imaging modalities are known and therefore detail description of their construction and operation is omitted here to avoid complicating the description of this disclosure. Iniewski et al. describe various imaging modalities in "Medical Imaging Principles, Detectors, and Electronics," John Wiley & Sons, Inc., New Jersey (2009), the disclosures of which are incorporated herein by reference in their entirety. In general, an imaging system may include an imaging source that provides some form of energy capable of penetrating tissues and an image acquisition device of some type that detects signals and converts signals to useful data for reconstruction of images using an algorithm. Medical imaging may provide anatomical, physiological, and functional information about tissues or organs, which is valuable in treatment planning and patient simulation to ensure accurate delivery of therapeutic dose for treatment. During treatment, an imaging system may be used in conjunction with the treatment machine to aid in patient setup and in guiding or monitoring treatment delivery. For example, in an x-ray radiotherapy system, a linear accelerator (LINAC) may include one or more imaging systems such as an imaging system including an On-board imager (OBI) available from Varian Medical Systems, Inc. of Palo Alto, Calif. An imaging system may include a designated imaging source and image acquisition device. Alternatively, an image acquisition device may be configured to acquire image signals using the treatment beam from the linear accelerator. In some embodiments, the energy of the radiation produced by the linear accelerator may be adjusted to provide beams suitable for image acquisition by an imager. The imaging system can also be a separated imaging device which performs imaging during treatment. For example, the imaging system can be a CT on rails, a mobile ultrasound device etc.

The reference image of the patient and/or the image of the individual may be either 2D images or 3D images. In some embodiments, the reference image of the patient is a 3D image and the image of the individual may be either a 2D image or a 3D image. Alternatively, the reference image of the patient is a 2D image and the image of the individual may be either a 2D image or a 3D image. A 2D image may be a projection image or a digital image reconstructed from image data acquired by an imaging system. A 2D image may be made up of an array of two-dimensional pixels (picture elements) each having an intensity value or gray shade value. The 2D array of pixels in the 2D image may correspond to an equal number of 3D voxels (volume elements) in the patient. The voxels have two dimensions equal to the pixels in the image plane, and the third dimension represents the slice thickness of a scan. A 3D image may be reconstructed from a series of 2D image data sets or from a volume image data set acquired by an imaging system. Volume rendering, reprojection or other suitable techniques known in the art may be used in volume reconstruction to present the image data in a 3D manner. By way of example, fan-beam CT (FBCT) or cone-beam CT (CBCT) systems may be used to acquire image data sets for 2D or 3D image reconstruction.

In some embodiments, the comparison of the medical image of the individual with the reference image of the patient may involve registration of the images of the individual and of the patient. The image registration can be performed automatically or manually. As used herein, the term "registration" refers to alignment between images of the same or different subjects, acquired using the same or different imaging modalities. Image registration establishes correspondence of spatial information in different images so that corresponding features can be related. In this disclosure, image registration and comparison can be between 2D (patient) and 2D (individual) images, 2D (patient) and 3D (individual) images, 3D (patient) and 2D (individual) images, and 3D (patient) and 3D (individual) images. The 2D or 3D images of the patient or individual can be obtained using the same imaging modality or different imaging modalities. Methods and algorithms for image registration of 2D or 3D images obtained using same or different imaging modalities are known in the art. Hajnal et al. describe various methods and algorithms for medical image registration in "Medical Image Registration," CRC Press LLC, 2001, the disclosures of which are incorporated herein by reference in their entirety.

In some embodiments, the comparison of the image of the individual with the reference image of the patient may include calculation of a similarity index between the image of the individual and the reference image of the patient. A greater similarity index value indicates a greater similarity between the images. A smaller similarity index value indicates more dissimilarity between the images. In this disclosure, because images compared are from either the same patient or from different patients, the similarity index value can be very high in cases where the images compared are from the same patient, or the index value can be very low in cases where the images compared are from different patients. A tolerance threshold can be defined in determining whether the images compared are from the same or different patients. If the similarity index value exceeds the defined tolerance threshold, a negating message can be generated to notify a user of the possibility of a wrong patient. If the similarity index value falls below the defined tolerance threshold, a confirming message can be generated to notify a user of a correct patient. Delivery of treatment dose may start or stay based on the calculated value of the similarity index.

Methods and algorithms for calculation of similarity index of images are available in the art including calculation of mutual information, cross correlation, and pattern intensity etc. These and other methods and algorithms are known in the art and therefore their detail description is omitted herein. In general, calculation of mutual information is a mathematical method of comparing two images. It is a pixel-wise method in calculating the similarity of two images. Mutual information of two random variables, in information theory, refers to the amount of information that one variable contains about the other. In this disclosure, mutual information can be qualitatively considered as a measure of how well one image explains the other. Correlation between two images (cross-correlation) is also a pixel-based method for feature detection. A pixel-wise cross-correlation can be computed using a mathematic matrix, which can be a measure for the degree of similarity of two images. Roshni V S et al. describe methods of calculation using mutual information and cross correlation in "Using Mutual Information and Cross Correlation as Metrics for Registration of Images," Journal of Theoretical and Applied Information Technology, 2006, pp. 474-481, the disclosures of which are incorporated herein in their entirety.

In some embodiments, the comparison of the medical image of the individual with the reference image of the patient may involve feature extraction and comparison of the features in corresponding regions of the two images. In pattern recognition, feature extraction is a form of dimensionality reduction and involves using an algorithm to detect and isolate various desired portions or shapes (features) of an image. Methods and algorithms for feature extraction are known in the art. In this disclosure, if the features in the images compared are classified as dissimilar, then the algorithm may conclude that the images are from different patients.

In some embodiments, anatomical landmarks or the shape and size of the patient's organ in both images can be segmented, extracted and compared. Anatomic landmarks are locations in an anatomy that can be detected in images with some certainty or confidence. By way of example, anatomic landmarks in the pelvis region of a human patient may include acetabulum, upper symphysis gap, trochanter major, pubic bone, or lower symphysis. Anatomic landmarks in the thorax region of a human patient may include cervix middle, axilla middle, thorax superior, thorax middle, or trachea bifurcation. Certain bones listed above may be highly characteristic for some patients, and certain features of the bones such as the diameter of the pelvic bone, the length of certain bones etc. can be calculated. If the anatomic landmarks or the shape or size of the patient's organ in both images compared are classified as similar, then the algorithm may conclude that the images are from the same patient.

In some embodiments, provided is a radiotherapy method which includes a patient identification process as an integral part of the radiotherapy. In implementing the method, an individual may be positioned in a treatment room for receiving radiotherapy. Before the treatment dose is delivered, a patient identification process is performed to verify the identity of the individual who has been positioned for treatment. The identification process either confirms or negates the individual to be the patient to whom the radiotherapy is intended. If the patient identification process confirms that the individual is the patient intended, the radiation beam may be turned on to start delivery of the treatment dose. If the patient identification process determines that the individual who has been positioned for radiotherapy is not the patient intended, the system may block the treatment beam and notify the user of a wrong patient. Advantageously, the patient identification process is an integral part of the treatment and unlikely to be omitted. Further, the images used for daily patient setup or positioning can be used to verify the identity of the individual, and therefore additional imaging system dedicated to patient identification is not required, although can be used.

In the provided radiotherapy method, patient identification may involve comparison of an image of the individual who has been set up for treatment with a reference image of the patient to whom the radiotherapy had been planned. The image of the individual and the reference image of the patient can be independently obtained using any suitable imaging modalities including such as X-ray radiography, computed tomography (CT) imaging, magnetic resonance imaging (MRI), positron emission tomography (PET) imaging, single photon emission computed tomography (SPECT) imaging, and ultrasound (US) imaging. The image of the individual and the reference image of the patient may be obtained using a same imaging modality. For example, the images of both the individual and the patient may be obtained using x-ray imaging, although the images may be acquired with different x-ray imaging machines at different locations. Alternatively, the medical image of the individual and the reference image of the patient may be obtained using different imaging modalities. For example, the medical image of the individual who has been set up to receive radiotherapy may be obtained using x-ray imaging, and the reference image of the patient may be obtained in a planning session using MRI or other imaging modalities, or vice versa.

The reference image of the patient and/or the image of the individual may be either 2D images or 3D images. By way of example, the reference image of the patient is a 3D image and the image of the individual may be either a 2D image or a 3D image. Alternatively, the reference image of the patient is a 2D image and the image of the individual may be either a 2D image or a 3D image. By way of example, fan-beam CT (FBCT) or cone-beam CT (CBCT) systems may be used to acquire image data for 2D or 3D image reconstruction.

Various methods and algorithms can be used in the comparison of the medical image of the individual with the reference image of the patient. Registration of 2D and/or 3D images of the same or different imaging modalities may be performed. For example, a similarity of index between the image of the individual and the reference image of the patient may be calculated and used in the comparison. A tolerance threshold may be defined in determining whether the images compared are from the same or different patients. For example, if the similarity index value exceeds the defined tolerance threshold, a negating message may be generated to notify a user of the possibility of a wrong patient. If the similarity index value falls below the defined tolerance threshold, a confirming message may be generated to notify a user of a correct patient. Delivery of treatment dose may start or stay based on the calculated similarity index value. The similarity index may be calculated using mutual information, cross correlation, pattern intensity, or any other suitable method or algorithms.

Alternatively, the comparison of the medical image of the individual with the reference image of the patient may be performed using feature extraction to compare the features in corresponding regions of two images. Anatomical landmarks or the shape and size of the patient's organ in both images can be segmented, extracted and compared. If for example, the anatomic landmarks or the shape or size of the patient's organ in both images compared are classified as similar, then the algorithm can conclude that the images are acquired from the same patient.

In some embodiments, a radiotherapy method adapted for fractionated treatment is provided. In the method, the total treatment dose is delivered in multiple sessions over time, and in each of the multiple sessions, patient identification using medical images is performed. In particular, the method may include a first treatment in a first session and a second treatment in a second session. In the first treatment a first verification is performed to verify whether a first individual is the patient to whom the first treatment is intended. The first verification includes obtaining an image of the first individual and comparing the image of the first individual with a first reference image of the patient to whom the treatment is intended. In the second treatment, a second verification is performed to verify whether the second individual is the patient to whom the second treatment is intended. The second verification includes obtaining an image of the second individual and comparing the image of the second individual with a second reference image of the patient to whom the treatment is intended. The first reference image and the second reference image of the patient can be the same and obtained in a planning session. Alternatively, the first reference image of the patient may be obtained in a planning session and the second reference image of the patient may be obtained during the first treatment in the first session when the first individual has been verified to be the patient intended. It should be noted that the term "first" or "second" are used herein for ease of description and is not intended to be literally limiting in a fractionated treatment including multiple sessions. For example, the second verification can be any subsequent verification at any of the subsequent treatment sessions. The second reference image may refer to a reference image for such second verification and can be a daily image such as an image obtained in a previous session during which the patient has been identified and confirmed. Images of the first individual, the second individual, and the patient can be independently obtained using X-ray radiography, computed tomography (CT) imaging, magnetic resonance imaging (MRI), positron emission tomography (PET) imaging, single photon emission computed tomography (SPECT) imaging, or ultrasound (US) imaging.

Exemplary embodiments are now described with reference to the figures. It should be noted that some figures are not drawn to scale, and are only intended to facilitate the description of specific embodiments. They are not intended as an exhaustive description or as a limitation on the scope of the invention.

FIG. 1 schematically illustrates an exemplary radiation system 100 which may be used to implement the method of this disclosure. The radiation system 100 may include a gantry 110, a patient support 120, and a control system 130. The control system 130 may be located outside a treatment room 102, within which the gantry 110 and the patient support 120 may be located. The gantry 110 may be rotatably supported by a stand 112 and contain various devices for beam generation and collimation. For example, the gantry 110 may contain an accelerator which may include an electron source and an accelerator guide configured to produce energetic electrons. The gantry 110 may also include a treatment head which may contain various devices configured to produce, shape, and monitor treatment beams. For example, the treatment head may include a target assembly adapted to produce x-ray radiation when impinged by energetic electron beams, a beam filter assembly adapted to even dose distribution across the radiation field, an ion chamber assembly configured to monitor the parameters of the radiation beam, a collimator assembly configured to define the overall size and shape of the beam, and so on. The gantry 110 may also support a multileaf collimator (MLC) operable to finely control the size and shape of the treatment beam. U.S. application Ser. No. 12/568,619, filed Dec. 18, 2009 and entitled "Beam Filter Positioning Device," describes various embodiments of a radiation system, the disclosure of which is incorporated herein by reference in its entirety.

The gantry 110 may support one or more imaging systems 114, 116. The imaging systems 114, 116 may aid in patient positioning or setup and in guiding and monitoring treatment dose delivery. The imaging systems 114, 116 may also aid in verifying patient identity as described in greater detail above. The imaging systems may include an MV imaging system 114 and a kV imaging system 116. The MV imaging system 114 may include an MV image detector that can be e.g. extended from and retracted into the base of the gantry 110. The MV image detector 114 may acquire image data using beams generated by the accelerator supported by the gantry 110. The kV imaging system 116 may include a kV imaging source and a kV image detector mounted e.g., on the sides of the gantry 110 and are movable. The image data acquired by the imaging systems 114, 116 may be processed using a suitable algorithm and the reconstructed images may be presented in a 2D or 3D manner on a display. The identity of the patient may be verified by comparing the daily patient images acquired by the imaging system 114, 116 with reference images provided to the control system 130.

The control system 130 controls the operation of the radiation system 100, preferably with a computer user interface 132. The control system 130 may include a computer comprising a memory and a processor such as a digital signal processor (DSP), a central processing unit (CPU), or a microprocessor (µP), and may be operated by a computer software interface such as a graphical user interface (GUI). The memory may store programs for operating the radiation system 100. The memory may store treatment plan information including such as the nature of the tumor in the patient, the treatment dose to be delivered, and the position and/or movement of the gantry 110 relative to the patient etc. In this disclosure, the memory may also store reference images of the patient and programs for performing patient identification. The processor may execute the patient identification programs using the reference images and images acquired in patient setup.

Figure 2:
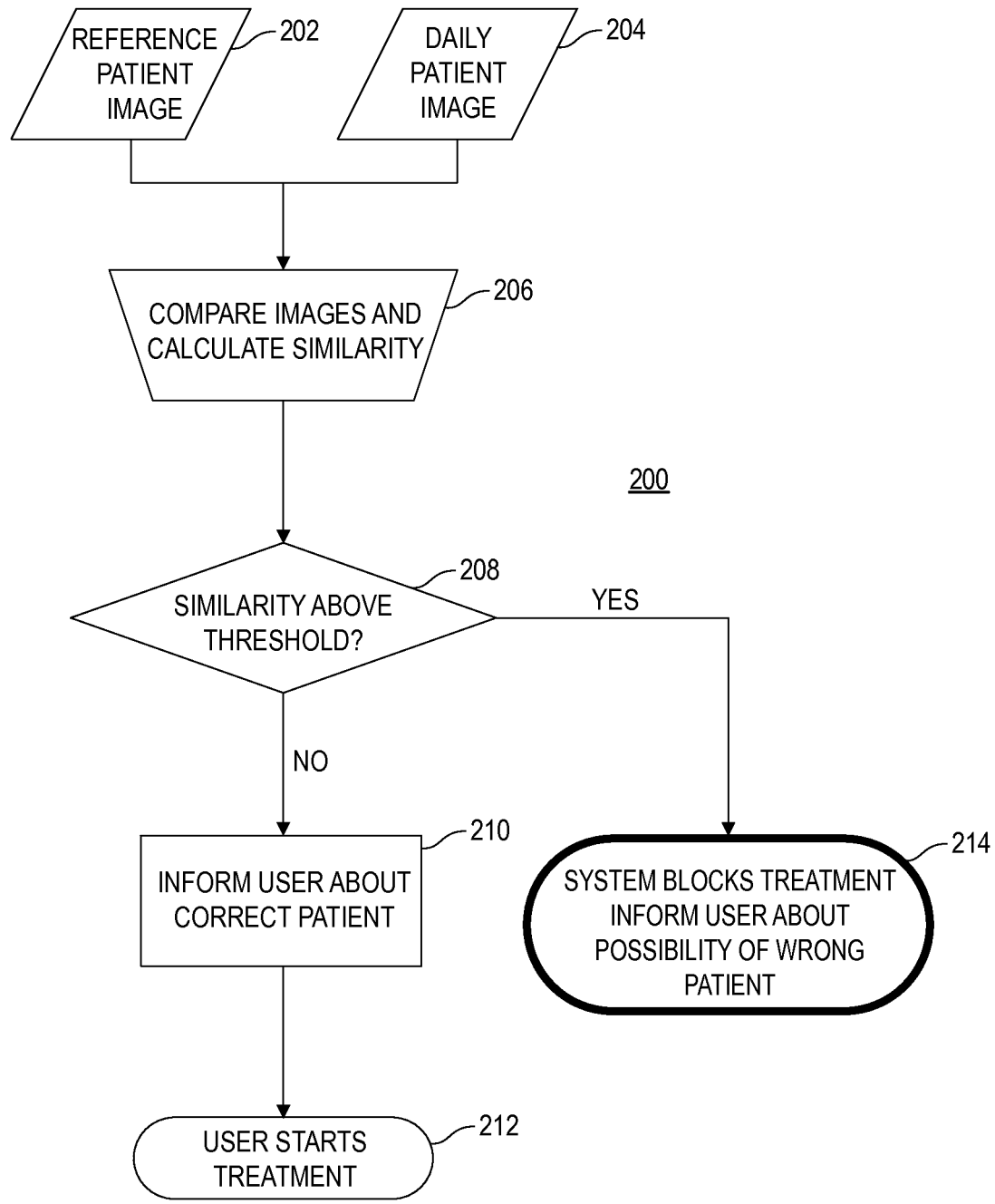
FIG. 2 is a flow chart illustrating the steps of a patient identification process in accordance with some embodiments of the disclosure.

FIG. 2 is a flow chart illustrating the steps of an exemplary patient identification process 200 in accordance with some embodiment of the disclosure. The reference patient image is provided at step 202 and the daily patient image is provided at step 204. The reference patient image may be obtained in a planning session or on the first treatment day of a fractionated radiotherapy. The daily patient image may be acquired using an imaging system when the patient is positioned or set up for treatment in a treatment room. The reference patient image and the daily patient image are compared at step 206 by e.g. calculating a similarity index or other suitable algorithms. At step 208, if it is determined that the similarity index calculated falls below a predefined tolerance threshold, a confirming message may be generated to inform a user that the correct patient has been set up (210), and the user may proceed to start the delivery of the treatment dose (212). If it is determined at step 208 that the calculated similarity index exceeds the predefined tolerance threshold, a negating message may be generated to inform the user about the possibility of a wrong patient, and the user may suspend the treatment or the system may automatically block the treatment (214). In some embodiments, the tolerance threshold may be dynamic and adaptive.

Figure 3:
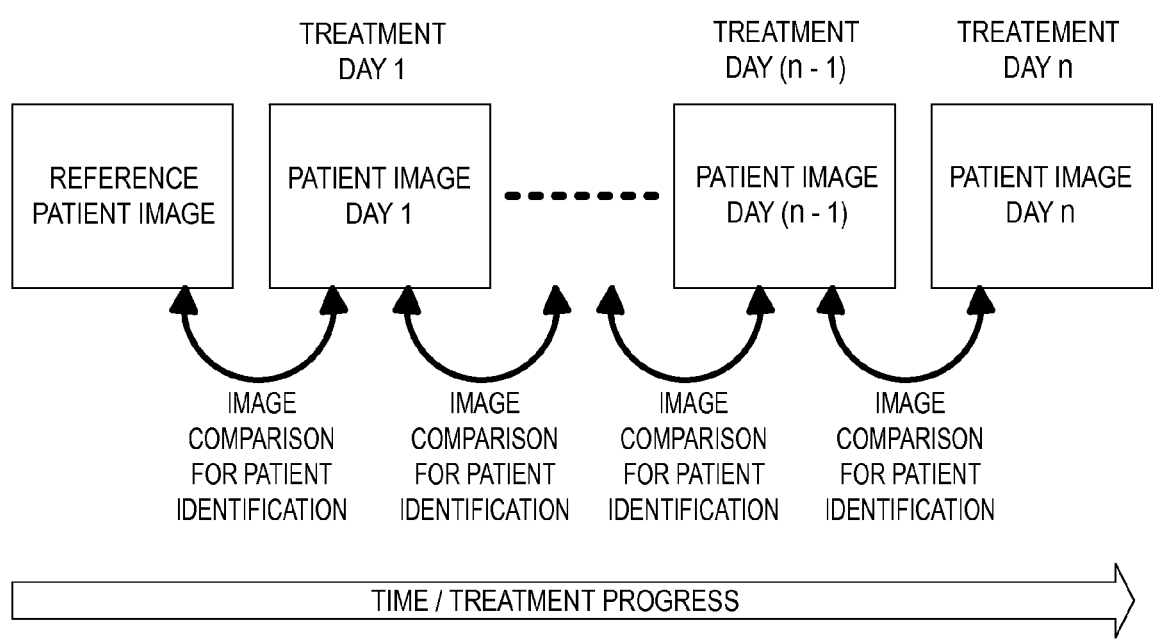
FIG. 3 is a block diagram illustrating a fractionated radiotherapy method in accordance with some embodiments of the disclosure.

FIG. 3 is a block diagram illustrating an exemplary fractionated radiotherapy method in accordance with some embodiments of the disclosure. The fractionated radiotherapy may include multiple sessions (n) over time (Treatment Day 1, . . . Treatment Day n−1, Treatment Day n), and each session may include a patient identification process using medical images. For example, in the first session on Treatment Day 1, a reference patient image may be compared with a daily patient image of Day 1. The reference patient image for the first session on Treatment Day 1 may be acquired in a treatment planning session prior to the radiotherapy. In the second session on Treatment Day 2, a reference patient image may be compared with a daily patient image of Day 2. The reference patient image for the second session on Treatment Day 2 may be obtained in the first session on Treatment Day 1 when the identity of the patient is confirmed and the patient treated. In the final session on Treatment Day n, the reference patient image from the session of Treatment Day (n−1) may be used to compare with the daily patient image acquired on Treatment Day n. Therefore, the reference images for patient identification in the fractioned radiotherapy may be the latest as the treatment progresses. Alternatively, the patient images from the different treatment days may be directly compared with the reference patient image acquired in the treatment planning session, rather than with the patient image of the previous treatment day.

A method for patient identification using medical images and a radiotherapy method incorporating patient identification as an integral part of the radiotherapy are provided Those skilled in the art will appreciate that various modifications may be made within the spirit and scope of the invention. All these or other variations and modifications are contemplated by the inventors and within the scope of the invention.

What is claimed is:

1. A method of verifying a patient identity, comprising the steps of:
   providing a reference image of a patient to whom a radiotherapy is intended;
   obtaining an image of an individual who is to receive the radiotherapy;
   comparing the obtained image of the individual with the reference image of the patient;
   confirming or negating the individual to be the patient intended based on the comparison of the obtained image of the individual with the reference image of the patient; and
   generating an output signal confirming or negating the verification, and/or warning signal if patient's variance exceeds a threshold,
   wherein the image of the individual is acquired in a treatment room in which the radiotherapy is to be provided; and
   the image of the individual is obtained using X-ray radiography, computed tomography (CT) imaging, magnetic resonance imaging (MRI), positron emission tomography (PET) imaging, single photon emission computed tomography (SPECT) imaging, or ultrasound (US) imaging.

2. The method of claim 1 wherein the reference image of the patient is an image of X-ray radiography, computed tomography (CT) imaging, magnetic resonance imaging (MRI), positron emission tomography (PET) imaging, single photon emission computed tomography (SPECT) imaging, or ultrasound (US) imaging.

3. The method of claim 1 wherein the image of the individual and the reference image of the patient are obtained using a same imaging modality or different imaging modalities.

4. The method of claim 1 wherein the image of the individual and/or the reference image of the patient are a 2D or 3D image.

5. The method of claim 1 wherein the comparison comprises calculation of a similarity index between the image of the individual and the reference image of the patient.

6. The method of claim 1 wherein the comparison comprises calculation of a similarity index between the image of the individual and the reference image of the patient using mutual information, cross-correlation, or pattern intensity.

7. The method of claim 1 wherein the comparison comprises extraction of features in the image of the individual and in the reference image of the patient and comparison of the extracted features.

8. The method of claim 1 wherein the comparison comprises segmentation of one or more anatomic landmarks in the image of the individual and in the reference image of the patient and comparison of the one or more anatomic landmarks.

9. The method of claim 1 wherein the image of the individual is acquired using an imaging system located in a treatment room.

10. The method of claim 1 wherein the first image of the individual is acquired using an imaging system that is coupled to a treatment machine.

11. A radiotherapy method, comprising the steps of:
    positioning an individual to receive radiotherapy on a treatment table;
    after the positioning of the individual, verifying identity of the individual to confirm or negate the individual to be a patient to whom the radiotherapy is intended; and
    performing the radiotherapy to the individual if the individual is confirmed to be the patient intended;
    wherein the verifying step comprises obtaining an image of the individual who has been positioned to receive radiotherapy and comparing the image of the individual with a reference image of the patient to whom the radiotherapy is intended; and
    wherein the image of the individual and/or the reference image of the patient are independently obtained using X-ray radiography, computed tomography (CT) imaging, magnetic resonance imaging (MRI), positron emission tomography (PET) imaging, single photon emission computed tomography (SPECT) imaging, or ultrasound (US) imaging.

12. The radiotherapy method of claim 11 wherein in the verifying step the image of the individual and the reference image of the patient are independently obtained using a same imaging modality or different imaging modalities.

13. The radiotherapy method of claim 11 wherein in the verifying step the image of the individual and/or the reference image of the patient are a 2D or 3D image.

14. The radiotherapy method of claim 11 wherein in the verifying step the comparison comprises calculation of a similarity index between the image of the individual and the reference image of the patient.

15. The radiotherapy method of claim 11 wherein in the verifying step the comparison comprises calculation of a similarity index between the image of the individual and the reference image of the patient using mutual information, cross-correlation, or pattern intensity.

16. The radiotherapy method of claim 11 wherein in the verifying step the comparison comprises extraction of features in the image of the individual and in the reference image of the patient and comparison of the extracted features.

17. The radiotherapy method of claim 11 wherein in the verifying step the comparison comprises segmentation of one or more anatomic landmarks in the image of the individual and in the reference image of the patient and comparison of the one or more anatomic landmarks.

18. A method of fractionated radiotherapy of a patient, comprising:
    a first treatment in a first session; and
    a second treatment in a second session; wherein
    the first treatment in the first session comprises a first verification of identity of a first individual, wherein the first verification comprises obtaining a daily image of the first individual and comparing the daily image of the first individual with a first reference image of the patient to whom the radiotherapy is intended, wherein the first verification is carried out in a treatment room in which the first treatment is to be provided; and the second treatment in the second session comprises a second verification of identity of a second individual, wherein the second verification comprises obtaining a daily image of the second individual and comparing the daily image of the second individual with a second reference image of the patient to whom the second treatment is intended, wherein the second verification is carried out in a treatment room in which the second treatment is to be provided.

19. The method of claim 18 wherein the first reference image of the patient is obtained in a planning session for the patient, and the second reference image of the patient is obtained in the first treatment in the first session during which the first individual is confirmed to be the patient to whom the radiotherapy is intended.

20. The method of claim 18 wherein the first reference image and the second reference image of the patient are both obtained in a planning session for the patient.

21. The method of claim 18 wherein the image of the first individual and the image of the second individual are independently obtained using X-ray radiography, computed tomography (CT) imaging, Cone Beam Computed Tomography (CBCT), magnetic resonance imaging (MRI), positron emission tomography (PET) imaging, single photon emission computed tomography (SPECT) imaging, or ultrasound (US) imaging.

22. The method of claim 18 wherein the first reference image and the second reference image of the patient are obtained in a treatment session prior to the first session.

* * * * *